(12) United States Patent
Maas

(10) Patent No.: US 6,416,782 B1
(45) Date of Patent: Jul. 9, 2002

(54) SELENIUM BOLUS FOR RUMINANTS

(75) Inventor: Kathleen Maas, Davis, CA (US)

(73) Assignee: Pacific Trace Minerals, Inc., Davis, CA (US)

(*) Notice: Subject to any disclaimer, the term of this patent is extended or adjusted under 35 U.S.C. 154(b) by 0 days.

(21) Appl. No.: 09/871,439

(22) Filed: May 31, 2001

(51) Int. Cl.[7] .......................... A23K 1/18; A61K 33/04
(52) U.S. Cl. ........................ 424/438; 424/702
(58) Field of Search ................... 424/702, 438

(56) References Cited

U.S. PATENT DOCUMENTS

| | | | |
|---|---|---|---|
| 4,044,119 A | 8/1977 | Carlson | 424/22 |
| 4,251,506 A | 2/1981 | Laby | 424/19 |
| 4,595,583 A | 6/1986 | Eckenhoff | 424/15 |
| 4,662,879 A | 5/1987 | Drake | 604/892 |
| 4,671,789 A | 6/1987 | Laby | 604/59 |
| 4,765,837 A | 8/1988 | Whitehead | 75/249 |
| 5,252,561 A | 10/1993 | Hornykeiwytsch | 514/23 |
| 5,985,314 A | 11/1999 | Porter | 424/438 |

OTHER PUBLICATIONS

Maas, Diagnosis and Management of Selenium–Responsive Diseases in Cattle, 1983, *Compend Contin Educ Pract Vet* 5: S393–399.

Maas, The Correlation Between Serum Selenium and Blood Selenium in Cattle, 1992, *J Vet Diagn Invest* 4: 48–52.

Maas, Intramuscular Selenium Administration in Selenium–Deficient Cattle, 1993, *J. Vet Int Med* 7: 342–348.

Eckenhoff, Extended Duration, Programmable, Rate Controlled Dosage Forms to Meet the Needs of the Animal Health Business, 1986, Mid–Year Animal Drug Meeting.

Eckenhoff, Veterinary Dosage Forms Using Princlipels of Osmosis, 1988, *Proceed Intern symp control Rel Bioact Mater* 15: 227–.

Eckenhoff, Osmotically Actuated Dosage Forms for Rate–Controlled Drug Delivery, 1987, *Pharm Tech*, 96–105.

Wilson, Evaluation of Multiple Reticulorumen Selenium Pellets as a Health Risk in Growing Hereford Steers, 1991, *Am J Vet Res* 52: 1866–70.

Coe, Randomized Field Trial to Determine the Effects of Oral Selenium Supplementation on Milk Production and Reproductive Performance of Holstein Heifers, 1993, JAVMA 202: 875–81.

*Primary Examiner*—Raymond Henley, III
(74) *Attorney, Agent, or Firm*—Law Office of Luann Cserr

(57) ABSTRACT

A bolus for oral administration of selenium to ruminants comprising 2% to 25% by weight of the trace mineral selenium in its elemental state and in particulate form, 70% to 97.5% by weight of an inert powdered weighting agent and, optionally, 0.25 to 5% by weight of an inert lubricant is provided.

27 Claims, 1 Drawing Sheet

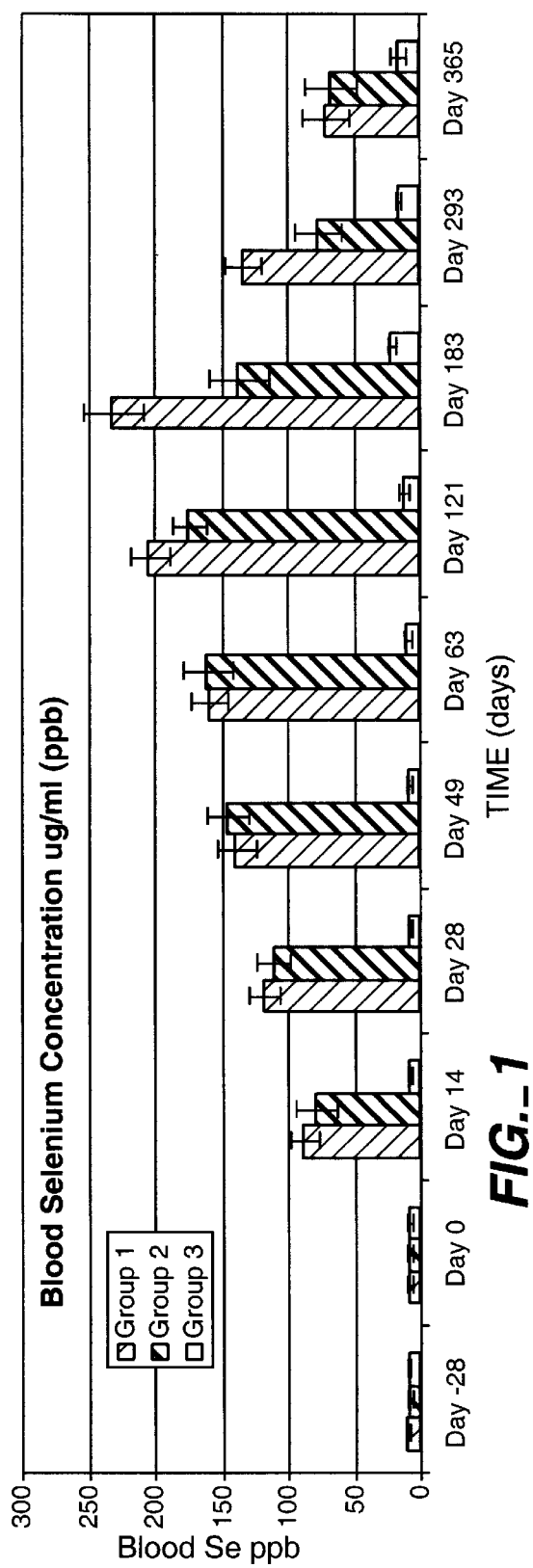
FIG._1
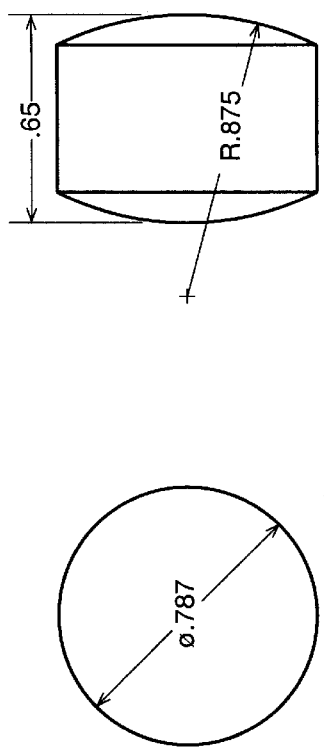
FIG._2a
FIG._2b

SELENIUM BOLUS FOR RUMINANTS

BACKGROUND

Certain trace minerals are essential nutrients for all animals, including cattle and other ruminants. See National Research Council: "Nutrient Requirements of Beef Cattle ", Washington DC, Natl Acad Sci, p 62–64, 1996. Such trace minerals include selenium, iodine, manganese, chromium, cobalt, copper, and zinc. Selenium, for example, is essential for the function of a number of critical mammalian selenoproteins, including for example the antioxidant enzyme glutathione peroxidase. In cattle, the selenium requirements are between 0.1 and 0.5 parts per million (ppm) of the diet on a dry matter basis. The Food and Drug Administration (FDA) has set an allowable supplementation level at 0.3 parts per million (ppm) of the diet for selenium and a maximum allowable level of supplemental selenium at 3 milligrams (mg) selenium per head per day for cattle.

Typically in cattle, selenium status is evaluated by measuring the selenium concentration in whole blood. See Maas, Diagnosis and Management of Selenium-Responsive Diseases in Cattle, 1983, *Compend Contin Educ Pract Vet* 5: S393–399; and Maas, The Correlation Between Serum Selenium and Blood Selenium in Cattle, 1992, *J Vet Diagn Invest* 4: 48–52. In cattle, blood selenium concentrations between 0.1 ppm to 1.0 ppm are considered normal, concentrations between 0.04 ppm to 0.1 ppm are considered marginally deficient, and concentrations below 0.04 ppm are considered frankly deficient. Marginally deficient blood selenium concentrations are indicative of potential subclinical disease symptoms and deficient blood selenium concentrations are indicative of potential clinical disease states. Most normal ruminants have blood selenium concentrations between 0.1 ppm and 0.3 ppm, whether or not their feed has been supplemented.

Selenium deficiency is the most commonly diagnosed disease problem in beef cattle in California. See 1997 Annual Report California Veterinary Diagnostic Laboratory System, pages 23–25, School of Veterinary Medicine, University of California, Davis (June 1998). Previous University of California studies have shown that 65% of beef cattle in Northern California and 64% of beef cattle in Central and Southern California are Selenium deficient. See Williams, 1988, "A survey into selenium deficiency in cattle in Northern California. " Master of Preventative Medicine Thesis. University of California, Davis. 55 pp; and Dunbar, 1988, "Preliminary Report on the Survey of Selenium Whole Blood Values of Beef Herds in Twelve Central and Coastal California Counties" pages 81–83 in *Selenium Contents in Animal and Human Food Crops Grown in California*. Cooperative Extension, University of California Division of Agriculture and Natural Resources, Publication 3330, Oakland, Calif. Both small and large ranching operations, which use pasture grazing on a continual basis, are affected by the grazing of cattle on selenium deficient ranch lands, which are prevalent in California and most other cattle producing states. National surveys by the USDA indicate that 63.6% of forage samples are deficient or marginal for selenium. "Trace mineral contents of harvested forages", USDA:APHIS, NAHMS Survey, October, 1996. Thus, cattle relying on this selenium deficient forage would require some level of selenium supplementation. Additionally, 18.2% of cattle in the United States were selenium deficient despite supplementation or producer's knowledge of supplementation methods. "Blood selenium levels in the U.S. beef cow/calf herd." USDA:APHIS, NAHMS Survey, October, 1996. In a survey of state veterinarians and state veterinary diagnostic laboratories, selenium-deficiency diseases were reported in 46 states and selenium deficiencies were reported to be an important livestock problem in 37 states. See, A. J. Edmondson, et al, "Survey of state veterinarians and state veterinary diagnostic laboratories for selenium deficiency and toxicosis in animals" Journal of the American Veterinary Medical Association, Vol. 202 (6), pp. 865–872, 1993. Thus, selenium supplementation continues to be necessary for the health, welfare, and productivity of grazing cattle in the United States.

Selenium deficient cattle typically exhibit decreased weight gains, decreased feed efficiency, chronic diarrhea, nutritional myodegeneration (white muscle disease), increased spontaneous abortion rates, reproductive losses due to retained placenta, illthrift, decreased immune function and increased susceptibility to infectious diseases. See Maas, Diagnosis and Management of Selenium-Responsive Diseases in Cattle, 1983, *Compend Contin Educ Pract Vet* 5: S393–S399. Cattle affected with trace mineral deficiencies, such as selenium deficiency, often have symptoms that mimic infectious or parasitic diseases and conditions such as diarrhea, lameness and illthrift. Commonly, animals with trace mineral deficiencies, such as selenium deficiency, are erroneously treated symptomatically by administration of antibiotics, parasiticides or other drugs that could leave residues in tissues.

Because of these conditions, the economic efficiency of raising cattle deficient in selenium or other trace minerals is decreased compared to raising cattle that are not deficient. For example, increased susceptibility to infectious diseases caused by lowered immune system function due to trace mineral deficiencies results in the increased use of antibiotics in animal health and production, which in turn has an adverse affect on profitability.

In the past, various methods have been used to increase the amount of trace minerals in animal diets. Animals confined in feeding operations such as poultry units, feedlots or dairies typically receive a formulated or mixed ration supplemented with the trace minerals required. Free ranging animals, those that graze on range lands, in foothill pastures, and on permanent pasture lands, for example, cannot obtain needed supplemental selenium or other trace minerals in this manner because it is cost prohibitive and impractical. Currently, salt-mineral mixes are employed to give grazing cattle supplemental dosages of selenium. The disadvantage to this approach is that it can often result in unpredictable and sporadic dosing, because the cattle can choose to ingest the mix, and also because of varying pasture conditions and varying climatic and seasonal conditions such as temperature and precipitation variations throughout the year. In addition, salt-mineral mixes are expensive due to labor costs and manufacturing costs.

Trace minerals have been administered to cattle by injection, but there are demonstrated limitations on the effectiveness of this method. For example, studies have shown that selenium administered by injection results in rapid increases in blood selenium concentration of very short duration, i.e., less than 45 days, and only partially meet the animals selenium nutrient requirements. See, Maas, et al, "Intramuscular selenium administration in selenium-deficient cattle." Journal of Veterinary Internal Medicine, vol. 7, pp.342–348, 1993.

Boluses are solid, ingredient release systems for oral administration in ruminants. The bolus remains in the gastrointestinal tract of the animal due to either its geometric shape or its density and mass. Boluses have been employed previously to deliver therapeutics, mineral supplements and a variety of other active ingredients to ruminants. For example, U.S. Pat. No. 4,765,837 issued Aug. 23, 1998 discloses a bolus for administration to a ruminant comprising a magnesium-based alloy and optionally trace elements including selenium up to 1% by weight. U.S. Pat. No. 4,044,119 issued Aug. 23, 1977 discloses an oral dosage medicinal composition for ruminants made by treating an admixture of milk solids and the medicament with an aldehydic agent to insolubilize the milk protein solids, granulating the product and compressing the granules under sufficient pressure to form a densified body having a specific gravity at least greater than about 1. U.S. Pat. No. 4,671,789 issued Jun. 9, 1987 discloses a controlled release composition for administering therapeutics to ruminants comprising a compressed bolus including the therapeutic and a non-tacky, free-flowing powdered, carrier material comprising a sucrose ester, polyglyceryl stearate or milk powder. U.S. Pat. No. 4,662,879 issued May 5, 1987 discloses a bolus composed of water soluble glass incorporating the mineral supplement contained in a plastic housing. U.S. Pat. No. 4,251,506 issued Feb. 17, 1981 discloses a controlled release composition for administering active ingredients to ruminants comprising the active agent in a matrix of water insoluble wax and at least two surfactants having an HLB value of 8.5 or less to avoid differential dissolution and non-uniform active agent release. U.S. Pat. No. 5,252,561 issued Oct. 12, 1993 discloses a controlled release bolus comprising the active ingredient, a wax, a weighting agent and a sugar, sugar alcohol, cellulose ether or a polyethylene glycol. U.S. Pat. No. 4,765,837 issued Aug. 23, 1988 discloses a bolus composes of compressed magnesium, zinc, and aluminum. U.S. Pat. No. 4,595,583 issued Jun. 17, 1986 discloses a bolus for the administration of a beneficial agent to ruminants, which comprises an osmotic pump with a semi-permeable membrane. U.S. Pat. No. 5,985,314 issued Nov. 16, 1999 discloses a bolus comprising a rosin matrix in which the active ingredient is dispersed and a non-soluble ballast material such as iron bound in the rosin matrix.

In addition, an iron-based, slow-release, selenium pellet made by Imperial Chemical Industries, Australia and called "Permasel" was in use in the United States (specifically California) from about 1980 to 1992. See, Wilson, Evaluation of Multiple Reticulorumen Selenium Pellets as a Health Risk in Growing Hereford Steers, 1991, *Am J Vet Res* 55: 247–50. These "Permasel" pellets exhibited unpredictable, inconsistent, wide variations in selenium release and they readily broke apart after manufacture and prior to use, for example, either during shipment or during storage, rendering them unusable. In addition, the Permasel pellets released daily concentrations of selenium in excess of those amounts approved by United States federal and state regulatory authorities, specifically, greater than 3 mg selenium per head per day.

It would be advantageous to provide a trace mineral supplement in bolus form for range and pasture managed cattle that is safe, capable of consistently providing the requisite amount of the trace mineral up to the regulated maximum and maintaining its form during transit and storage prior to use and is cost effective and practical for cattle ranchers to use. It would be particularly advantageous to provide a selenium supplement in bolus form that could accomplish the foregoing.

SUMMARY OF THE INVENTION

It has been found that to obtain consistent and predictable release of trace minerals, in particular selenium, from solid boluses, four variables must be evaluated and integrated. The four variables are: (1) the concentration of the trace mineral, (2) the particle size of the trace mineral, (3) the pressure under which the bolus is formed, and (4) the surface area of the bolus, which is a function of the size and shape of the bolus.

Surprisingly, it has been found that consistent and reliable release of selenium up to the regulated maximum limit can be achieved when the bolus comprises particulate selenium in concentrations of between 2% and 25% by weight and having an average diameter from 20 microns to 1,500 microns combined under 2,000 to 50,000 pounds per square inch (psi) with an inert metal powder to form a bolus having a mass of between 10 to 50 grams and a final bolus size between 10 mm and 40 mm in diameter and between 10 mm and 30 mm in height and a final density of 6.1 to 6.4 g/cm$^3$. It has been found that boluses having the foregoing characteristics will release a consistent, reliable amount of selenium in an amount not greater than 3 mg per head per day. In addition, in has been found that such boluses maintain their shape after manufacture and do not break apart prior to use, for example during transit or storage.

Accordingly, in one aspect, the invention relates to a bolus for oral administration of selenium to ruminants comprising a solid, compressed dosage form composed of about 2% to about 25% by weight of selenium in particulate form, about 70% to about 97.5% by weight of an inert, powdered, weighting agent and optionally about 0.25 to about 5% by weight of an inert lubricant. Preferably, the selenium. comprises from about 5 to about 15% by weight, most preferably from about 8 to about 12% by weight. The particulate selenium should have an average diameter in the range of 20 to 1,500 microns, most preferably in the range of 70 to 500 microns, when combined with the inert, powdered weighting agent under between 2,000 and 50,000 pounds per square inch (psi) to form the bolus. The mass of the bolus should be in the range of about 10 to about 50 grams, preferably in the range of about 25 to about 35 grams, most preferably about 30 grams. The size of the bolus should be in the range of 10 to 40 millimeters (mm) in diameter and in the range of 10 and 30 mm in height, more preferably in the range of 15 to 25 mm in diameter and in the range of 15 to 25 mm in height, and, most preferably, approximately 20mm in diameter and approximately 16.5 mm in height. The selenium particles should have an average diameter in the range of about 70 to about 500 microns when combined with inert metal powder under about 18,000 to about 25,000 psi, given a size range from 25 to 35 grams (g) and a final density in about 6.1 to about 6.4 g/cm$^3$. Table 1 below sets forth the range of specifications for the particular boluses of the invention.

By ruminant, I mean, in particular, cattle, sheep and goats. By "dosage form", I mean a form that results in release of the active ingredient in a consistent and reliable dosage. In shape, the bolus can be spherical, cylindrical, elongated cylindrical, flat cylindrical or donut. Each of these shapes, having heights and diameters in the ranges set forth, will provide the requisite surface area to release the selenium active ingredient in an amount not greater than 3.0 mg per head per day.

Inert powdered weighting agents include those that have a density high enough to maintain the bolus in the stomach, despite the animal's natural regurgitation mechanisms. Such density depends on the size of the bolus and its surface area and the composition of the density-imparting weighting agent. Generally, a density of at least about 3.0 g/cm$^3$ is required to maintain the bolus in the ruminant's stomach. Accordingly, exemplary powdered weighting agents comprising, for example, nickle, tin, hydroxyapatite, barium sulfate, barium titanate, tin oxide, iron silicate, iron oxides, sponge iron, atomized base iron, stainless iron, alloyed base iron and calcium phosphates, all of which have specific densities of at least about 3.0 g/cm$^3$ can be employed. Preferred weighting agents are powdered metals. Particularly preferred weighting agents include iron, sponge iron, or powdered metal iron particles, for example Ancorsteel 1000B® (Hoeganaes, Riverton, N.J.).

In the choice of weighting agents, particulate size is not a critical parameter. The weighting agent should have a density high enough to maintain the bolus in the animal's stomach, generally at least about 3.0 g/cm$^3$, and should be able to mix well with the elemental selenium and with any optional lubricant added. Such optional lubricants will now be described.

Optionally, an inert, biologically acceptable material may be included as a lubricant to aid in the formation of the bolus during manufacture. Exemplary inert biological materials include surfactants, such as Tween 80, zinc stearate, sodium lauryl sulphate, EBS, and other waxes such as Acrawax C® (N,N'-ethylenebisstearamide. Acrawax C® is appropriately used in concentrations from 0.25 to 5% in the final mixture. The concentration of other lubricants should likewise range from 0.25 to 5% in the final mixture.

DESCRIPTION OF THE DRAWINGS

FIG. 1 is a graphic representation of the results of the experiment detailed in Example 2.

FIG. 2a is a plan view of the bolus made as detailed in Example 1 and FIG. 2b is a side view of that bolus. As shown in the FIG. 2a, the diameter is the bolus measures 0.787 inches, and as shown in FIG. 2b, the height of the bolus measures 0.65 inches and the radius of curvature of the top surface of the bolus measures 0.875 inches.

DETAILED DESCRIPTION

It has been found that consistent and reliable release of selenium can be achieved in a compressed dosage form that is composed of particulate selenium, in its elemental form, in concentrations of between 2% and 25% by weight and having an average diameter from 20 microns to 1,500 microns when combined with an inert metal powder in a concentration of between 70% and 98% by weight and, optionally, an inert lubricant in a concentration of between 0.25% to 2% by weight. The bolus is formed by mixing the components to achieve a uniform mixture and compressing the mixture under pressure of between for example 2,000 to 50,000 pounds per square inch (psi). To release the requisite concentration of selenium and to maintain the bolus in the stomach of the ruminant, the bolus should have a mass of

TABLE 1

Bolus Specifications Table

| FACTOR AND UNITS | RANGE | PREFERRED RANGE | MOST PREFERRED RANGE |
|---|---|---|---|
| Selenium % in bolus | 2–25% | 8–12% | 10% |
| Selenium particle size, in microns | 20–1500 | 70–500 | 70–500 |
| Powdered iron | 70–98% | 86–92% | 89.25–90% |
| Wax | 0.25–5% | 0.25–2% | 0.75% |
| Manufacturing pressure, in psi | 2,000–50,000 | 18,000–25,000 | 20,000–23,000 |
| Density, in g/cm$^3$ | 4.5–7.5 | 6.1–6.4 | 6.2–6.3 |
| Diameter, in mm | 10–40 | 15–25 | 20 |
| Height, in mm | 10–30 | 15–25 | 16.5 |
| Shape | Sphere, flat cylinder, donut, elongated cylinder | Sphere, flat cylinder, donut, elongated cylinder | Flat cylinder |

In another aspect, the invention comprises a method of treating ruminants with a selenium supplement comprising orally administering to the ruminant a bolus having about 2% to about 25% by weight of the trace mineral selenium in particulate form, about 70% to about 98% by weight of an inert powdered weighting agent, and optionally, about 0.25 to about 5% by weight of an inert lubricant.

In yet another aspect, the invention comprises a process for the preparation of a trace mineral bolus for oral administration in ruminants containing about 2% to about 25% by weight of selenium, about 70 to about 98% by weight of an inert powdered weighting agent and about 0.25% to about 5% of an inert, biologically acceptable lubricant. The method comprises mixing the trace mineral with the weighting agent and, optionally, the lubricant in a suitable mixer, for example a double cone mixer, or alternatively a double bell mixer, and applying to the mixture pressure in the range of about 2,000 to about 50,000 psi until a solid mass is formed. Suitable tools for applying pressures in the range specified include a 45 ton Dorst compacting press. Other appropriate tools for mixing the components and for applying pressure in the requisite range to form the bolus are well known to those of skill in the art.

between 10 to 50 grams, more preferably between 20 and 40 grams and most preferably about 30 grams and a size between 10 mm and 40 mm in diameter and between 10 mm and 30 mm in height and having a density of between 4.5 and 7.5 g/cm$^3$, preferably between 6.1 to 6.4 g/cm$^3$, most preferably between 6.2 and 6.3 4 g/cm$^3$.

Preferably, the bolus should comprise elemental selenium, from about 8% to about 12% by weight, an inert weighting agent, from about 86% to about 91.75% by weight and an inert lubricant, from about 0.25 to about 2% by weight. Most preferably, the bolus will comprise 10% by weight of elemental selenium.

The inert weighting agent can be selected from silver, iron, nickle, lead, antimony, tin, hydroxyapatite, barium sulfate, barium titanate, alumina, tin oxide, rutile titanium dioxide, calcium tungstate, iron tungstate, iron tungstate, iron silicate, iron aluminum oxide, iron oxides, calcium molybdate and calcium phosphate, and should be in powdered form. Powdered iron, such as Ancorsteel 1000B® (Hoeganaes, Riverton, N.J.), is preferred.

The inert lubricant can be selected from a surfactant, such as Tween®, Brij®, and sodium lauryl sulphate and a wax, such as is N,N'-ethylenebisstearamide (AcrawaxC®), which is a reaction product of ethylenediamine and stearic acid. AcrawaxC® is preferred.

In a most preferred form, the bolus for oral administration of selenium to ruminant animals comprises a solid, compressed dosage form having a size and shape capable of oral administration to the ruminant animal. It contains about 10% by weight elemental selenium in the form of particulates, which have an average diameter in the range of 20 microns to 1,500 microns, about 89.25% by weight powdered iron and, about 0.75% by weight wax, preferably N,N'-ethylenebisstearamide.

The invention also includes a process for the preparation of a selenium bolus for oral administration to ruminant animals composed of the steps of mixing the elemental selenium with the weighting agent and, optionally, the lubricant in a suitable mixer until a uniform mixture of components is obtained and applying to the resultant mixture pressure in the range of 18,000 to 25,000 psi, preferably under about 20,000 to 23,500 psi, until the mixture of components form a solid mass.

The invention further includes a method for supplementing the diet of a ruminant animal with a selenium supplement, by orally administering to the ruminant animal a bolus containing the components described above in the amount described above, and formed as described above.

In the Examples set forth in detail below, a process for making a selenium bolus suitable for administration to ruminant animals is described. Briefly, selenium in its elemental and powdered form having particle sizes in the range of 70 microns to 1,500 microns are mixed with powdered iron and with the inert lubricant AcrawaxC® (in the specified concentrations in a double cone mixer and mixed until uniform to the eye. The uniform mixture of the three ingredients was then compressed under 20,000 psi pressure using a Dorst 45 ton compacting tool. The resulting bolus had a mass of 30 grams and a density of 6.26 g/cm$^3$. The shape and size of the final product is shown in FIG. 2. However, a variety of different shapes could be used. These shapes include, but are not limited to, spheres, elongated cylinders, and donut shapes.

In Example 2, boluses made in accordance with the process detailed in Example 1 were administered to one group of heifers and another group of heifers were orally administered the sustained-release selenium bolus, Dura-Se® (Schering-Plough Corp.). A third group were not administered any selenium supplements. Blood samples for selenium analysis were taken and the results compared. The results demonstrated that blood selenium concentrations were significantly lower ($P<0.001$) in the control group (Group 3) compared with the groups receiving supplementation of selenium by either bolus (Groups 1 and 2). Heifers receiving the 10% elemental selenium bolus (Group 2) had lower blood selenium concentrations on days 14, 28 and 121 and slightly higher selenium concentrations on days 49 and 63, compared to heifers in Group 1 (Dura-Se® bolus), but these differences were not significant. There was no physical evidence of excess selenium intake observed in any of the treatments groups at any time during the study These results, which are shown graphically in FIG. 1, demonstrated that oral administration of the 10% elemental selenium bolus of Example 1 provides adequate, predictable and consistent supplemental selenium comparable to that provided by the currently approved oral selenium product, Dura-Se®.

EXAMPLE 1

Process of Making Selenium Bolus

The selenium bolus is comprised of three basic ingredients: (1) elemental selenium, (2) powdered metal (iron), and (3) a lubricant. These materials are mixed and then processed, under pressure, to form a solid bolus.

The elemental selenium powder used should have particle sizes ranging from 20 microns to 1,500 microns in diameter. The optimum particle size for the elemental selenium is from 70 to 500 microns, which was the size employed here. The powdered metal used has compression characteristics compatible with the requirements for the finished bolus. For purposes of this Example, Ancorsteel 1000B® was used. Ancorsteel 1000B® is 99.3% iron, has an apparent density of 2.88 g/cm$^3$, and has a compressibility of 6.80 g/cm$^3$ (at 30 tsi with 1.0% zinc stearate).

The sieve analysis for Ancorsteel 1000B® is +40=0%, −40/+60=trace,−60/+100=12.9%, −100/+200=37%, −200/+325=25.4%, and −325=24.7%. The inert lubricant used was Acrawax C®, which is (N,N'-ethylenebisstearamide, a reaction product of ethylenediamine and stearic acid).

The elemental selenium, Ancorsteel 1000B and Acrawax® described above should be mixed in the following optimum concentrations by weight: (1) elemental selenium =8–12%, (2) Ancorsteel 1000B®=86–91.75%, and (3) Acrawax C®=0.25–2.0%. In this example, the concentrations used were: (1) elemental selenium =10%, (2) Ancorsteel 1000B®=89.25%, and (3) Acrawax C®=0.75%. The three ingredients were combined in a double cone mixer and mixed until uniform to the eye.

The uniform mixture of the three ingredients was then compressed to form the final product. The tool used for this compression was a Dorst 45 ton compacting tool. The tooling components used were mounted in a master die set, which is part of the Dorst 45 compacting press. These components comprised the upper and lower punches, which are designed to produce the bolus in the final size and shape as shown in FIG. 2. The manufacturing pressures for compacting the bolus should be in the range of about 2,000 to about 50,000 pounds per square inch (psi), more preferably in the range of about 18,000 to about 25,000 psi. In this example, pressure was applied at 20,000 psi. To form the bolus, the die was filled with the uniform mixture made as described above and the upper and lower punches of the master die set closed. Pressure at 20,000 psi was then applied for a length of time sufficient to compact the ingredients into a solid mass. The die set was then opened and the solid mass bolus ejected. The process described above resulted in a bolus weighing 30 grams, measuring 20 mm in diameter and 17 mm in height, and having a density of 6.26 g/cm$^3$.

The shape of the product in its most simple design is shown in FIG. 2. The cylindrical shape shown in FIG. 2 has a diameter of 0.787 inches (20 mm) as shown in FIG. 1 and a height of 0.65 inches (16.5 mm) as shown in FIG. 2b. Further, its top surface has a radius of curvature of 0.875 inches. However, as set forth previously, a variety of different shapes could be used. These shapes include, but are not limited to, spheres, flat cylinders, elongated cylinders, and donut shapes.

EXAMPLE 2

Administration of Selenium Bolus in Cattle

Fifty-five beef heifers were used in this experiment. All heifers had been weaned for at least 28 days prior to the beginning of the experiment. The heifers were stratified by age and body weight at weaning and were randomly assigned to one of three treatment groups. All groups were maintained on a foothill range in a selenium-deficient natural environment in California and did not receive any additional nutritional supplements. The cattle were managed by standard cattle operating procedures and subjected to standard husbandry procedures, including health observations, vaccinations, anthelminthic administration (dewormings) and measuring individual body weights.

The 18 heifers in Group 1 were orally administered the sustained-release selenium bolus, Dura-Se® (Schering-Plough Corp.). This bolus releases 3 mg of selenium per day, after an initial 14-day lag period during which the osmotic pump is becoming fully charged. See, J. B. Eckenhoff, "Extended duration, programmable, rate controlled dosage forms to meet the needs of the animal health business", Proceedings of the 1986 Mid-Year Animal Drug Meeting, sponsored by the Animal Health Institute, Tampa, Fla., Oct. 14–17, 1986. J. B. Eckenhoff, et al, "Osmotically actuated forms for rate-controlled drug delivery", Pharmaceutical Technology, June, pp 96–102, 1987. F. Theeuwes, et al, "Update '87", Pharmaceutical Technology, June, pp 102–105, 1987. J. B. Eckenhoff, "Veterinary dosage forms using principles of osmosis", Proceedings International Symposium Controlled Release Bioactive Material, vol. 15, page 227, 1988. A subgroup of Group 1 (subgroup 2X, see Table 1) was given a second Schering-Plough Dura-Se® bolus on day 121 and the data for this subgroup only is shown in FIG. 1, for days 183, 293, and 365.

The 18 heifers in Group 2 were orally administered one bolus each, made as described in Example 1, on day 0. This bolus was comprised of 10% elemental selenium, 89.25% Ancorsteel 1000B, and 0.75% Acrawax C®, compressed at 20,000 psi into the circular tablet shape shown in FIG. 2 and measuring 20 mm (0.787 inches) in diameter and 17 mm (0.65 inches) in height, and having a density of 6.26 g/cm$^3$, as described in Example 1. The nineteen heifers in Group 3 received no treatment.

Blood samples (EDTA vacutainer tubes) for selenium analysis were taken from all 3 groups at days −28, 0, 14, 28, 49, 63, 121, 183, 293, and 365. The Dura-Se® bolus releases 3 mg selenium per day after an initial equilibration period of 14 days. See, J. B. Eckenhoff, "Extended duration, programmable, rate controlled dosage forms to meet the needs of the animal health business", Proceedings of the 1986 Mid-Year Animal Drug Meeting, sponsored by the Animal Health Institute, Tampa, Fla., Oct. 14–17, 1986.

Therefore, after the day 0 administration of the treatments, additional blood samples were taken from group 1 animals (the Dura-Se® bolus group) at days 42, 77 and 134. Because of the equilibration time lag of the group 1 bolus, the recorded blood selenium concentration data for group 1 animals was adjusted to the sample time 14 days ahead through experimental day 121. For example, the 14-day blood selenium concentration data in the results for group 1 animals was actually from the 28-day samples. The 28-day group 1 data is from samples taken on day 42 of the experiment, and the 49-day group 1 blood selenium data is from samples taken on day 63. The 63-day blood selenium data for group 1 was from blood samples taken on day 77 and the 121-day data for group 1 was from samples taken on day 134. Samples days 183, 293, and 365 were the same for all groups. The groups were maintained together as a single management unit, on the same pastures and did not receive any forage supplements, mineral supplements or salt. On day 121, one-half of the heifers in group 1 (the Dura-Se® bolus group) were administered a second Dura-Se® bolus, in order to maintain an internal positive control group that was being supplemented with 3 mg selenium per head per day.

Blood selenium concentration was measured by inductively coupled argon plasma emission spectroscopy following the procedures detailed in Tracy, Continuous Flow Vapor Generation for Inductively Coupled Argon Plasma Spectrometric Analysis. Part I. Selenium, 1990, *J Assoc Off Anal Chem* 73: 404–410. The heifers were examined on each sampling date for physical evidence of alopecia, lameness, coronitis or other physical indications of excess selenium intake. The results were examined by repeated measures analysis of variance (ANOVA). Differences were considered significant at the P<0.05 level. The results are set forth in Table 2 below as mean blood selenium concentration.(std dev) in ng/ml (parts per billion) and in FIG. 1. The control heifers remained Se deficient for the entire treatment period (below 40 ppb [parts per billion] is considered Se deficient), whereas blood selenium concentrations in the two treatment groups compared favorably with each other and were in acceptable ranges, reaching up to about about 200 ppb by day 121.

TABLE 2

Blood selenium concentration (mean ± std dev) in heifers given Se on day 0 or left as controls. Blood Se concentration reported as ng/ml (ppb; parts per billion).

| Treatment Group | −28 | 0 | 14 | 28 | 49 | 63 | 121 | 183* | 293* | 365* |
|---|---|---|---|---|---|---|---|---|---|---|
| Group 1 Schering-Plough bolus N = 18 | 8.9$^a$ ± 1.4 | 8.7$^a$ ± 2 | 87.7$^a$ ± 10.8 | 118.2$^a$ ± 12 | 138.4$^a$ ± 13.9 | 159.3$^a$ ± 13.6 | 203.2$^a$ ± 14.8 | 1X 114$^a$ ± 16 2X 231$^b$ ± 22.7 | 1X 34.8$^a$ ± 8.8 2X 133$^b$ ± 13.4 | 1X 24.8$^a$ ± 6.6 2X 71.4$^b$ ± 17.8 |
| Group 2 10% Se bolus N = 18 | 8.5$^a$ ± 2 | 8.6$^a$ ± 2 | 78.4$^a$ ± 16.5 | 110.3$^a$ ± 12.8 | 145$^a$ ± 16.4 | 160.4$^a$ ± 18.8 | 173.8$^b$ ± 12.6 | 137$^a$ ± 23 | 76$^c$ ± 17.9 | 67$^b$ ± 18.9 |
| Group 3 Control Heifers N = 19 | 8.8$^a$ ± 1.4 | 8.0$^a$ ± 2.1 | 7.3$^b$ ± 1.2 | 7.1$^b$ ± 1.7 | 7.8$^b$ ± 2.8 | 9.2$^b$ ± 2.7 | 11.9$^c$ ± 4.6 | 21.2$^c$ ± 2.8 | 15.5$^d$ ± 2.7 | 15.1$^a$ ± 5.6 |

*On day 121 Group 1 animals were randomly split into two subgroups. One subgroup of Group 1, the subgroup denoted "2X", received a second Schering-Plough Dura-Se ® bolus and thus continued to be supplemented with 3 mg Se per day. The other subgroup, denoted "1X", received no further Se supplementation. Means with varying superscript letters (a, b, c, d) in each column were significantly different (P < 0.05).

There was no physical evidence of excess selenium intake observed in any of the treatment groups at any time during the study. Blood selenium concentrations were significantly lower (P<0.001) in the control group (Group 3) compared with the groups receiving supplementation of selenium by either bolus (Groups 1 and 2). Heifers receiving the 10% elemental selenium bolus (Group 2) had lower blood selenium concentrations on days 14, 28 and 121 and slightly higher selenium concentrations on days 49 and 63, compared to heifers in Group 1 (Dura-Se® bolus), but these differences were not significant.

These results demonstrate that oral administration of the 10% elemental selenium bolus of Example 1 provides adequate, predictable and consistent supplemental selenium comparable to that provided by the currently approved oral selenium product, (Dura-Se®). These results are illustrated graphically in FIG. 1.

I claim:

1. A bolus for oral administration of selenium to ruminant animals comprising:
   a solid, compressed dosage form containing:
   (a) 2% to 25% by weight of elemental selenium, said elemental selenium being in the form of particulates, said particulates having an average diameter in the range of 20 microns to 1,500 microns; and
   (b) 70% to 98% by weight of an inert weighting agent, said solid compressed dosage form having a density sufficient to maintain said bolus in the stomach of the animal and a surface area sufficient to achieve release of not greater than 3.0 mg per head per day of selenium.

2. The bolus according to claim 1 wherein said elemental selenium comprises 10% by weight.

3. The bolus according to claim 1, additionally comprising 0.25 to 5% by weight of an inert lubricant.

4. The bolus according to claim 3 wherein said solid compressed dosage form contains 8% to 12% by weight of elemental selenium, 86% to 91.75% by weight of inert weighting agent and 0.25 to 2% by weight lubricant.

5. The bolus according to claim 4 wherein said inert lubricant is selected from the group consisting of a surfactant and a wax.

6. The bolus according to claim 5 wherein said inert lubricant is a surfactant and said surfactant is selected from the group consisting of Tween 80, zinc stearate and sodium lauryl sulphate.

7. The bolus according to claim 5 wherein said inert lubricant is a wax and said wax is N,N'-ethylenebisstearamide.

8. The bolus according to claim 4 wherein said inert weighting agent is selected from the group consisting of nickle, tin, hydroxyapatite, barium sulfate, barium titanate, tin oxide, iron silicate, iron oxide, sponge iron, atomized base iron, stainless iron, alloyed base iron and calcium phosphate.

9. The bolus according to claim 8 wherein said inert weighting agent comprises powdered iron.

10. The bolus according to claim 1 wherein said solid, compressed dosage form has a mass of between 20 and 40 grams.

11. The bolus according to claim 1, wherein said solid, compressed dosage form has a density between 6.1 and 6.40 g/cm³.

12. A bolus for oral administration of selenium to ruminant animals comprising a solid, compressed dosage form having a size and shape capable of oral administration to said ruminant animal and containing:
   (a) 2% to 25% by weight of elemental selenium, said elemental selenium being in the form of particulates, said particulates having an average diameter in the range of 20 microns to 1,500 microns;
   (b) 70% to 97.75% by weight of an inert weighting agent in powdered form, said inert weighting agent being selected from the group consisting of nickle, tin, hydroxyapatite, barium sulfate, barium titanate, tin oxide, iron silicate, iron oxides, sponge iron, atomized base iron, stainless iron, alloyed base iron and calcium phosphate; and,
   (c) 0.25 to 5% by weight of an inert lubricant selected from the group consisting of a surfactant and a wax.

13. The bolus accordingly to claim 12 wherein said inert weighting agent comprises sponge iron and said lubricant comprises a wax.

14. The bolus according to claim 13 wherein said wax comprises N,N'-ethylenebisstearamide.

15. A bolus for oral administration of selenium to ruminant animals comprising a solid, compressed dosage form having a size and shape capable of oral administration to said ruminant animal and containing:
   (a) 8% to 12% by weight of elemental selenium, said elemental selenium being in the form of particulates, said particulates having an average diameter in range of 20 microns to 1,500 microns;
   (b) 86% to 91.75% by weight of an inert weighting agent in powdered form, said inert weighting agent being selected from the group consisting of nickle, tin, hydroxyapatite, barium sulfate, barium titanate, tin oxide, iron silicate, iron oxide, sponge iron, atomized base iron, stainless iron, alloyed base iron and calcium phosphate; and,
   (c) 0.25% to 2% by weight of an inert lubricant selected from the group consisting of a surfactant and a wax.

16. The bolus according to claim 15 wherein said elemental selenium comprises 10% by weight.

17. A bolus for oral administration of selenium to ruminant animals comprising a solid, compressed dosage form having a size and shape capable of oral administration to said ruminant animal and containing:
   (a) 10% by weight elemental selenium, said elemental selenium being in the form of particulates, said particulates having an average diameter in the range of 20 microns to 1,500 microns;
   (b) 89.25% by weight powdered iron; and,
   (c) 0.75% by weight N,N'-ethylenebisstearamide.

18. A process for the preparation of a trace mineral bolus for oral administration in ruminant animals containing 2% to 25% by weight of elemental selenium, 70 to 97.75% by weight of an inert powdered weighting agent and 0.25% to 5% of an inert, biologically acceptable, lubricant, said process comprising:
   (a) mixing said elemental selenium with said weighting agent and said lubricant in a suitable mixer until a uniform mixture of components is obtained and
   (b) applying to said mixture pressure in the range of 18,000 to 25,000 psi until a solid mass bolus is formed.

19. The process according to claim 18 wherein said bolus comprises:
   (a) 8% to 12% by weight of elemental selenium, said elemental selenium being in the form of particulates, said particulates having an average diameter in the range of 20 microns to 1,500 microns;
   (b) 86% to 91.75% by weight of an inert weighting agent in powdered form, said inert weighting agent being selected from the group consisting of nickle, tin, hydroxyapatite, barium sulfate, barium titanate, tin oxide, iron silicate, iron oxide, sponge iron, atomized base iron, stainless iron, alloyed base iron and calcium phosphate; and, (c) 0.25% to 2% by weight of an inert lubricant selected from the group consisting of a surfactant and a wax.

20. The process according to claim 19 wherein said bolus comprises:
   (a) 10% by weight elemental selenium, said elemental selenium being in the form of particulates, said particulates having an average diameter in the range of 20 microns to 1,500 microns;
   (b) 89.25% by weight powdered iron; and,
   (c) 0.75% by weight N,N'-ethylenebisstearamide.

21. The process according to claim 20 wherein said bolus has a density in the range of 6.1 to 6.4 g/cm$^3$.

22. A method for supplementing the diet of a ruminant animal with a selenium supplement comprising orally administering to said ruminant animal a bolus containing 2% to 25% by weight of elemental selenium in particulate form, 70% to 97.75% by weight of an inert powdered weighting agent and optionally 0.25 to 5% by weight of an inert lubricant.

23. The method according to claim 22 wherein said bolus comprises:
   (a) 8% to 12% by weight of elemental selenium, said elemental selenium being in the form of particulates, said particulates having an average diameter in the range of 20 microns to 1,500 microns;
   (b) 86% to 91.75% by weight of an inert weighting agent in powdered form, said inert weighting agent being selected from the group consisting of nickle, tin, hydroxyapatite, barium sulfate, barium titanate, tin oxide, iron silicate, iron oxide, sponge iron, atomized base iron, stainless iron, alloyed base iron and calcium phosphate; and
   (c) 0.25% to 2% by weight of an inert lubricant selected from the group consisting of a surfactant and a wax.

24. The method according to claim 23 wherein said bolus comprises:
   (a) 10% by weight elemental selenium, said elemental selenium being in the form of particulates, said particulates having an average diameter in the range of 20 microns to 1,500 microns;
   (b) 9.25% by weight powdered iron; and,
   (c) 0.75% by weight N,N'-ethylenebisstearamide.

25. The bolus according to claim 17 wherein said bolus has a maximum release rate of 3 mg per day.

26. The process according to claim 21 wherein said bolus has a maximum release rate of 3 mg per day.

27. The method according to claim 21 wherein said bolus has a maximum release rate of 3 mg per day.

* * * * *